United States Patent
Mattchen

(10) Patent No.: US 10,383,658 B2
(45) Date of Patent: Aug. 20, 2019

(54) VECTOR COMPRESSION SYSTEM

(71) Applicant: POLY-4 GROUP, LP, Austin, TX (US)

(72) Inventor: Terry M. Mattchen, Austin, TX (US)

(73) Assignee: POLY-4 GROUP, LP, Austin, TX (US)

(*) Notice: Subject to any disclaimer, the term of this patent is extended or adjusted under 35 U.S.C. 154(b) by 367 days.

(21) Appl. No.: 14/762,902

(22) PCT Filed: Mar. 13, 2014

(86) PCT No.: PCT/US2014/025653
§ 371 (c)(1),
(2) Date: Jul. 23, 2015

(87) PCT Pub. No.: WO2014/160024
PCT Pub. Date: Oct. 2, 2014

(65) Prior Publication Data
US 2015/0374410 A1   Dec. 31, 2015

Related U.S. Application Data

(63) Continuation-in-part of application No. 13/829,031, filed on Mar. 14, 2013, now Pat. No. 9,345,469.

(51) Int. Cl.
*A61B 17/56* (2006.01)
*A61B 17/58* (2006.01)
(Continued)

(52) U.S. Cl.
CPC .......... *A61B 17/68* (2013.01); *A61B 17/0401* (2013.01); *A61B 17/0642* (2013.01);
(Continued)

(58) Field of Classification Search
CPC combination set(s) only.
See application file for complete search history.

(56) References Cited

U.S. PATENT DOCUMENTS 3,166,072 A   1/1965 Sullivan, Jr. .................. 606/153
4,565,193 A   1/1986 Streli ............................. 128/92
(Continued)

FOREIGN PATENT DOCUMENTS

DE   8709353   9/1987
EP   0591991   5/1998
(Continued)

OTHER PUBLICATIONS

International Search Report and Written Opinion Issued in PCT/US2014/025653, dated Jul. 18, 2014.

*Primary Examiner* — Sameh R Boles
(74) *Attorney, Agent, or Firm* — Norton Rose Fulbright US LLP

(57) ABSTRACT

This disclosure includes surgical anchors and related devices and methods that can be used for surgical bone fracture fixation. Some embodiments involve the use of a polymeric cored braided suture that can be held in place by anchors implanted or inserted into bone on each side of a fracture. In some embodiments, the present anchors can be secured into the bone while maintaining high tension (e.g., relative to certain prior art methods) in the suture during the deployment process. Some embodiments can provide for tensioning (e.g., using a polymeric cored braided suture) to compress the fracture and hold the bone in place, functioning as though the suture has sewn the bone (e.g., fragments or portions) together. This can, for example, provide rigid fixation of a fracture which may be important for healing to occur. The tension preload can provide compression to maintain fixation in the face of tensile and shear loads applied to the bone (e.g., as a result of movement and weight bearing).

17 Claims, 6 Drawing Sheets

(51) Int. Cl.
  *A61B 17/064* (2006.01)
  *A61B 17/84* (2006.01)
  *A61F 2/30* (2006.01)
  *A61B 17/68* (2006.01)
  *A61B 17/04* (2006.01)
  *A61B 17/06* (2006.01)
  *A61B 17/00* (2006.01)

(52) U.S. Cl.
  CPC .. *A61B 17/06166* (2013.01); *A61B 17/06123* (2013.01); *A61B 17/842* (2013.01); *A61B 2017/0046* (2013.01); *A61B 2017/00398* (2013.01); *A61B 2017/0409* (2013.01); *A61B 2017/0414* (2013.01); *A61B 2017/0459* (2013.01); *A61B 2017/0641* (2013.01)

(56) References Cited

U.S. PATENT DOCUMENTS

| | | | |
|---|---|---|---|
| 4,838,254 A | 6/1989 | Gauthier | 606/75 |
| 5,258,015 A | 11/1993 | Li et al. | 606/232 |
| 5,586,985 A | 12/1996 | Putnam et al. | 606/69 |
| 5,961,521 A | 10/1999 | Roger | 606/73 |
| 6,013,077 A | 1/2000 | Harwin | 606/72 |
| 6,086,608 A | 7/2000 | Ek et al. | 606/232 |
| 6,093,190 A | 7/2000 | Mattchen | 606/74 |
| 6,755,831 B2 | 6/2004 | Putnam et al. | 606/69 |
| 7,267,682 B1 | 9/2007 | Bender et al. | 606/219 |
| 8,029,535 B2 | 10/2011 | Ortiz et al. | 606/232 |
| D691,720 S | 10/2013 | Cheney et al. | D24/145 |
| 2004/0220574 A1* | 11/2004 | Pelo et al. | A61F 2/0063 606/232 |
| 2005/0010228 A1 | 1/2005 | Medoff | 606/74 |
| 2005/0192581 A1 | 9/2005 | Molz et al. | 606/74 |
| 2006/0058802 A1 | 3/2006 | Kofoed | 606/75 |
| 2008/0004624 A1 | 1/2008 | Olroyd | 606/70 |
| 2009/0054982 A1 | 2/2009 | Cimino | 623/13.11 |
| 2011/0022099 A1 | 1/2011 | Ashman | 606/331 |
| 2011/0160766 A1 | 6/2011 | Hendren et al. | 606/151 |
| 2012/0130422 A1 | 5/2012 | Hootstein | 606/228 |
| 2013/0184768 A1 | 7/2013 | McIff et al. | 606/301 |
| 2013/0315963 A1 | 11/2013 | Erneta et al. | 424/400 |
| 2015/0094762 A1 | 4/2015 | Spenciner | 623/13.14 |

FOREIGN PATENT DOCUMENTS

| | | |
|---|---|---|
| EP | 1016377 | 4/2006 |
| EP | 1844715 | 10/2007 |
| FR | 2638630 | 5/1990 |
| FR | 2722975 | 2/1996 |
| FR | 2991569 | 12/2013 |
| WO | WO 98/37825 | 9/1998 |
| WO | WO 03/007839 | 1/2003 |
| WO | WO 2005/124187 | 12/2005 |
| WO | WO 2010/014119 | 2/2010 |

* cited by examiner

VECTOR COMPRESSION SYSTEM

CROSS-REFERENCE OF RELATED APPLICATIONS

This application is a national phase application under 35 U.S.C. § 371 of International Application No. PCT/US2014/025653 filed Mar. 13, 2014, which claims the benefit of priority to U.S. patent application Ser. No. 13/829,031, filed Mar. 14, 2013, the entire contents of each of which are incorporated by reference here in their entirety.

BACKGROUND OF THE INVENTION

A. Field of Invention

The present invention involves devices and methods related to surgical bone fixation technology.

B. Description of Related Art

Bone is a remarkable material, and rare in its potential to heal completely following significant trauma. This potential is, at least in part, a product of the continuous remodeling that living bone undergoes and may only be fully realized under conditions conducive to healing. The goals of the treatment of fractures can include reduction of the fracture to as close to normal anatomy as possible and/or fracture fixation that allows the bone to heal without complications. Better fixation typically promotes more rapid healing and thus allows earlier load bearing.

Bone generally can heal in two ways, which may be referred to as primary and secondary healing. Primary healing is typically achieved by tunneling of osteoclasts; cells specialized to resorb bone, across the line of the fracture. This is followed by growth of blood vessels down the length of the tunnel and deposition of bone filling in the tunnel walls by osteoblasts, cells specialized in depositing bone. In this fashion, new bone is produced that spans the fracture and replaces the broken bone. Secondary healing typically proceeds by the formation of a callus (e.g., a large mass of collagen and granulation tissue). During this process, there is resorption of strained areas of bone adjacent to the fracture. Woven bone is deposited in the callus in an unstructured manner and is then remodeled by osteoclasts and osteoblasts to produce the healed bone.

Primary healing is desirable, in part, due to its lower risk of complications and potential for shorter healing time. However, primary healing is typically possible only with substantial, if not absolute, stabilization of the fracture (e.g., by fixation). Proper fixation may also reduce the risk of non-union (e.g., where the fracture fails to heal and fibrous tissue is instead produced). The reasons for this largely depend on the structure of the bone and/or the way in which the bone cells respond to the loads that are applied to the bone (e.g., relative movement of bone fragments is highly undesirable).

Current technology for internal fixation of fractures includes a variety of approaches. The most common of these include screws, compression plates, medullary nails, staples, and wires. These devices may be made from a variety of materials whose properties are compared to bone in Table 1 below. Screws are usable in fractures where it is possible to drill a hole at an angle to the fracture so that the screw compresses the fracture as it is tightened. Compression plates can be affixed to a fractured bone in a way that spans the fracture and compresses two pieces of bone together (e.g., by placing the plate itself under tension). Medullary nails are rods driven into the medullary cavity of fractured long bones and can serve to align the bone fragments while only partially bearing the load. Staples are typically driven into bone so that they span a fracture and provide fixation, but may not be capable of providing significant compression. Metal wires have been used to apply initial compression to fractures by tightening the metal wire (e.g., in various lacing methods).

TABLE 1

Properties of Implant Materials and Bone

| Material | Elastic Modulus GPa | Yield Stress MPa | Ultimate Stress MPa | Fatigue Endurance MPa |
|---|---|---|---|---|
| Ti—6Al—4V | 110 | 800 | 965 | 414 |
| 316L SS | 200 | 700 | 965 | 345 |
| Co—Cr—Mo (cast) | 210 | 450 | 655 | 310 |
| Co—Cr—Mo (forged) | 210 | 896 | 1207 | 414 |
| Bone | 17 | 130 | 150 | 34 |

SUMMARY

All of these methods described above have shortcomings despite their clinical usefulness. Metal fixation devices generally suffer from a mismatch in elasticity between the device and the bone that a device is compressing. This can result in a loss of compression with very minor amounts of bone resorption or device stretching. Nails, screws, wire, and plates are all typically prone to fatigue-induced failure which can lead to the need for further surgical intervention. Plates can also produce a stress-shielding effect, whereby the load is taken by the plate instead of the bone causing disuse-induced resorption and weakening of the bone. Screw holes may act as stress risers in bone, leading to an increased risk of pathologic fractures. Aside from purely mechanical effects described above, plates and rods require relatively large incisions and disrupt either the periosteum or the medullary blood supply when it is needed most. Due to these shortcomings, there is an ongoing need for better fixation methods.

Some embodiments of the present devices and methods address some of the deficiencies of the previously-known fracture fixation technology. Some of the present embodiments are configured to include, be used with, or involve the use of, a polymeric cored braided suture held in place by anchors implanted in bone on each side of a fracture. The polymeric cored braided suture may be tensioned so as to compress the fracture and hold it in place (e.g., as shown in FIG. 1), functioning as though it has sewn the bone fragments back together such as, for example, in a truss-like configuration spanning the fracture. This can provide rigid fixation of the fracture; which is typically considered to be essential for primary healing to take place. Simultaneously, the tension preload on the suture can provide compression which maintains fixation in the face of tensile and shear loads applied to the bone as a result of movement and weight bearing.

In some of the present embodiments, four suture legs may be included in a pattern, and two such patterns may be applied per fracture (one pattern on either side of a bone). If each suture leg is set to induce ten pounds of force across the anchors, for example, eighty pounds of cumulative force act to compress the bone fragments together during the healing process.

Any anchor in this type of system may be challenged by the simultaneous needs to:

1. maximize securement of the anchor into the bone, while
2. maintaining very high tensions in the suture as it is wound around the anchor.

Achieving a simultaneous optimum of these two goals presents an inherent conflict that can also be addressed by and with the present embodiments.

One example of a suture suitable for use in or with at least some of the present embodiments is a prior art cable described in U.S. Pat. No. 6,589,246. A suture described in this patent comprises of a nylon monofilament core surrounded with a high-strength ultra-high molecular weight polyethylene braided jacket, giving it strength comparable to the highest strength multicore steel cable while being much more flexible, fatigue resistant and abrasion resistant. At least some embodiments of the present anchors may be capable of distributing the suture load into the bone while holding up to 100 pounds in shear. At least some embodiments of the present deployment instrument are designed to be used by a surgeon to place anchors and set the compressive load in the suture. Thus, the present deployment instruments may be rather complex (relative, for example, to prior art devices for deploying nails and screws) in that a single instrument can supply both the anchors and suture in a disposable cartridge. At least some of the present deployment instructions are packaged or configured as an easily-handled compact unit, and/or may be configured for endoscopic use. In at least some embodiments, the present deployment instructions have simple controls in order to be workable in a surgical environment. Additionally, at least some embodiments of the present deployment instruments are configured to:

Be able to drive the anchor in a controlled condition or manner,

Be able to tension the suture to attain the desired compressive force,

Be able to set the anchor while maintaining the compressive force across a fracture so that the suture does not slip, and/or Incorporate a disposable cartridge that attaches to a power unit with the suture and anchors housed in the cartridge.

In summary, several embodiments of surgical anchors operable for securing surgical cable are disclosed. Some of the present surgical anchors comprise an essentially rotated "E" shaped staple having three prongs and a bridge. In at least some embodiments, the three prongs are substantially parallel to each other, and one of the prongs (e.g., the middle one of the three) may define or be coaxial with a longitudinal axis of the staple. In some embodiments, the bridge is unitary with and substantially perpendicular to each of the three prongs and may define a bridge axis (e.g., through proximal ends of the two lateral prongs) that may be perpendicular to the longitudinal axis of the staple.

In some embodiments, the three prongs include a first outer or lateral prong, a middle prong, and a second outer or lateral prong. A first space may be defined by the void between the first outer prong and the middle prong. The first space can be characterized by a first width, which may be defined by the perpendicular distance between the first outer prong and the middle prong. A first arch may be defined by the first outer prong, the middle prong and the bridge. A second space may be defined by the void between the second outer prong and the middle prong. The second space can be characterized by a second width, which may be defined by the perpendicular distance between the second outer prong and the middle prong. A second arch may be defined by the second outer prong, the middle prong and the bridge. The first width may be equal to the second width.

In some embodiments, the first arch has a first shape that includes an arc of a conic cross section and the second arch has a second shape that also includes an arc of a conic cross section. In some embodiments, the first shape is substantially identical to the second shape.

In some embodiments, the first outer prong has a first length and the middle prong has a middle length that is substantially equal to the first length. In some embodiments, the second outer prong has a second length that is substantially equal to both the first length and the middle length. Alternatively, the second length may be shorter than the first length and/or the middle length (e.g., by at least a distance equal to the second width).

In some embodiments, the "E" shaped staple is flat (e.g., the three prongs may all lie in a single plane). In other embodiments, the bridge is curved such that the "E" shaped staple (e.g., the bridge) has a cross-sectional shape that includes an arc of a conic cross section (e.g., of a circle, an ellipse, or a parabola). Either of the flat or shaped embodiments may have equal length prongs, or may have two long prongs and one short prong, as described above.

Any of the present embodiments may include a surgical cable comprised of a polymer core and a braided jacket.

In some embodiments of the present surgical anchors, each of the three prongs has a proximal end coupled to the bridge and a distal end extending away from the bridge, and the distal ends of at least two of the prongs comprise cutting portions configured to be inserted into bone. In some embodiments, the distal ends of all three of the prongs comprise cutting portions configured to be inserted into bone. In some such embodiments, the cutting portion of at least one of the prongs comprises first and second faces that are tapered relative to each other to define a cutting edge. In some embodiments, the cutting edge is substantially perpendicular to the prong. In some embodiments, the cutting edge is disposed at a non-perpendicular angle relative to a longitudinal axis of the respective prong. In some embodiments, the cutting edge lies in a plane that substantially bisects the respective prong. In some embodiments, the cutting portion of at least one of the prongs comprises first, second, and third faces that taper relative to each other to define a cutting point. In some embodiments, the cutting point is substantially centered on the distal end of the prong. In some embodiments, the first and second faces are not symmetrical. In some embodiments, the first and second faces are symmetrical.

In some embodiments of the present surgical anchors, at least one of the prongs has portion in which a transverse dimension of the prong decreases in a direction from the proximal end to the distal end. In some embodiments, at least one of the prongs has a portion in which a transverse dimension of the prong increases in a direction from the proximal end to the distal end.

In some embodiments, of the present surgical anchors, at least one of the bridge and a prong comprises an edge that is chamfered or beveled. In some embodiments, the edge is adjacent to one of the first and second spaces between prongs.

Some embodiments of the present methods comprise: providing a surgical anchor (e.g., comprising: a bridge; and a first outer prong, a middle prong, and a second outer prong, the prongs extending away from the bridge substantially parallel to each other; where the first outer prong and the middle prong are longer than the second outer prong); threading a suture between the first outer prong and the middle prong; inserting the first outer prong and the middle prong into a bone such that the second outer prong is does not extend into the bone; wrapping the suture around the middle prong; and inserting the first outer prong and middle prong further into the bone such that the suture is disposed between the middle prong and second outer prong and the second outer prong contacts the bone.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF ITEMS IN THE FIGURES

100—anchor
110—polymeric cored braided suture
120—fractured bone
130—vector compression system
200—vector compression anchor
210—outer prong
220—middle prong
230—arch
240—bridge
300—vector compression anchor
310—long outer prong
320—long inner prong
330—short outer prong
350—cross section of a polymeric cored braided suture (110) shown in phantom
400—flat vector compression anchor
410—curved vector compression anchor
415—chamfered and/or a beveled edge
420—first face of the flat vector compression anchor (400)
430—second face of the flat vector compression anchor (400)
440—cutting edge of the flat vector compression anchor (400)
450—first face of the curved vector compression anchor (410)
460—second face of the curved vector compression anchor (410)
470—third face of the curved vector compression anchor (410)
480—cutting point of the curved vector compression anchor (400)
500—short prong (320) of the flat vector compression anchor (400) contacting and/or cutting into the polymeric cored braided suture (110)
510—short prong (320) of the curved vector compression anchor (410) clearing the polymeric cored braided suture (110)
600—exemplary deployment instrument
610—impulse motor
620—tensioning knob
630—tension release button
640—ratchet mechanism
650—suture drum
660—anchor magazine

BRIEF DESCRIPTION OF THE FIGURES

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiments depicted in the figures.

DETAILED DESCRIPTION OF ILLUSTRATIVE EMBODIMENTS

Figure 1A:
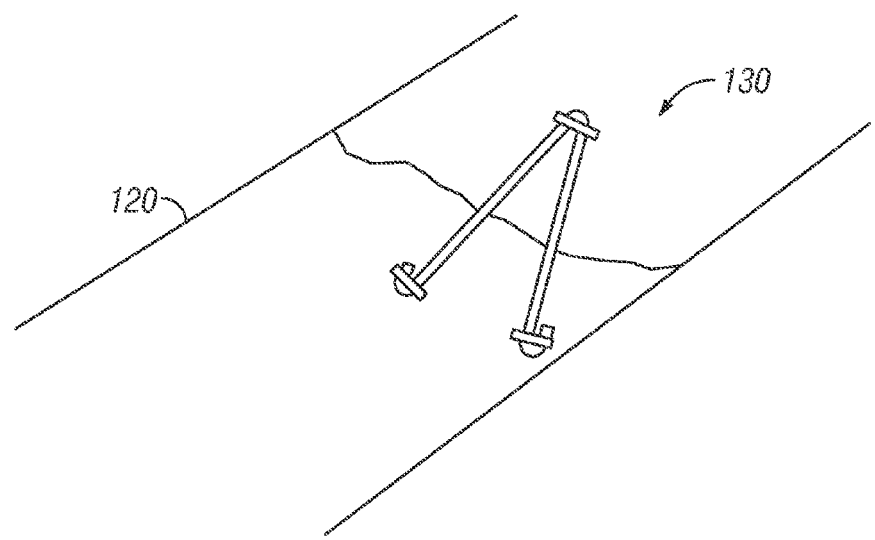
FIG. 1: Illustrates an example of a suitable environment and use of one embodiment of the present vector compression systems (130). A fractured bone (120) is "sewn" together using a series of polymeric cored braided sutures (110) and anchors (100) placed on either side of the bone fracture as shown in FIG. 1A.
FIG. 1B shows an enlarged, close-up view of the securement site. Although a simple "V" shaped pattern is shown in the figure, an I, N or W pattern may be used as well.
Figure 1B:
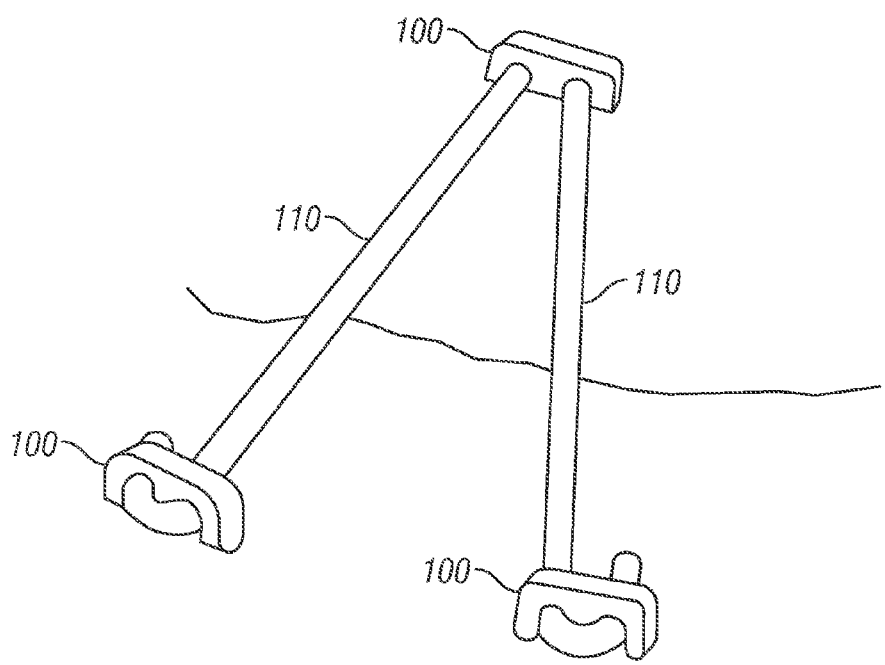

The vector compression system (130) of FIG. 1 illustrates a basic environment (e.g., at or over a fracture of a bone (120)) in which the present embodiments may be implemented. In the example shown, a fractured bone (120) is "sewn" together using a series of polymeric cored braided sutures (110) and anchors (100) placed on either side of the bone fracture site. The present disclosure presents several embodiments (e.g., 200, 300, 300, 400, 410) of novel designs for the anchors (100) that can be used in such a system. As noted above, the suture (110) can, for example, comprise the prior art cables disclosed in U.S. Pat. No. 6,589,246.

Figure 2:
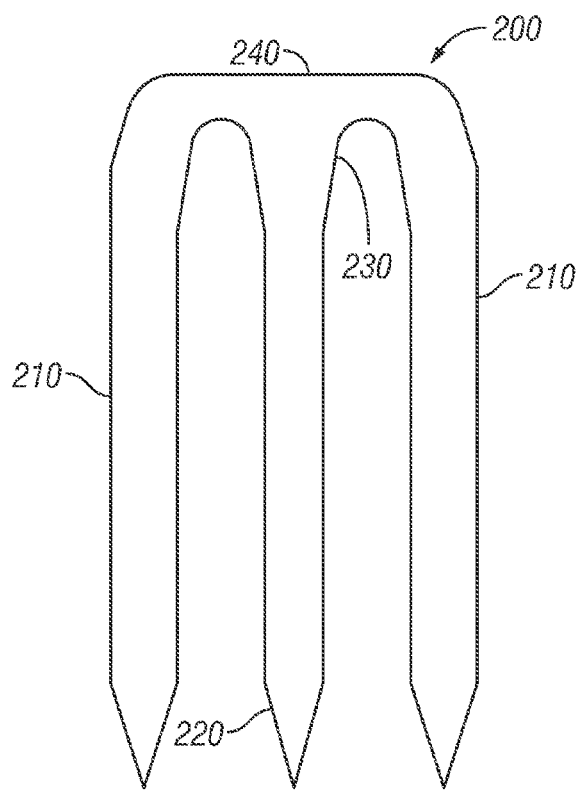
FIG. 2: A side view of the "E" shaped geometry of an embodiment of a basic anchor (200) is shown. The basic anchor (200) has three prongs (210, 220) of equal length. An arch (230), defined by the space between the bridge (240) and each of the prong pairs, serves to further secure the polymeric cored braided sutures (110) when the basic anchor (200) is fully driven into the bone. The shape of the arch (230) is generally a conic section (e.g., an arc of a circle, ellipse, or parabola).

FIG. 2 shows the "E" shape of the first embodiment of basic anchor (200). In this embodiment, the anchor (200) includes two outside (210) prongs and one middle (220) prong with all three prongs having substantially equal lengths, and a bridge (240) extending between and coupled to (e.g., unitary with) the prongs. In contrast, the vector compression anchor (300) of FIG. 3 has one long outside outer prong (310) that is equal in length to a long middle or inner prong (320), and one short outside prong (330) that is shorter than each of the outer prong (310) and the inner prong (320). In these embodiments (200 and 300), an arch (230) is defined by the space between adjacent prongs and the bridge (240) and can be rectangular, but a curve such as is defined by an arc of a conic cross-section (e.g., a circle, ellipse or parabola) may be desirable in certain embodiments, such as, for example, to more closely fit the cross-sectional shape of the suture (110). In both embodiments of FIGS. 2-3, the spacing between the prongs as well as the arch (230) is tailored to be smaller than the diameter of the suture (110) to compress the polymeric cored braided suture (110) when the suture (110) is disposed in an arch (230) such as when the anchor (200, 300) is fully driven into the bone (120). In some embodiments, the present anchors have a maximum width (in the direction of the bridge) of between 2 mm and 4 mm (e.g., 2.5-3 mm), and a length of between 4 mm and 7 mm (e.g., 5 mm) and/or have a width:length ratio of 1:2.

Figure 3:
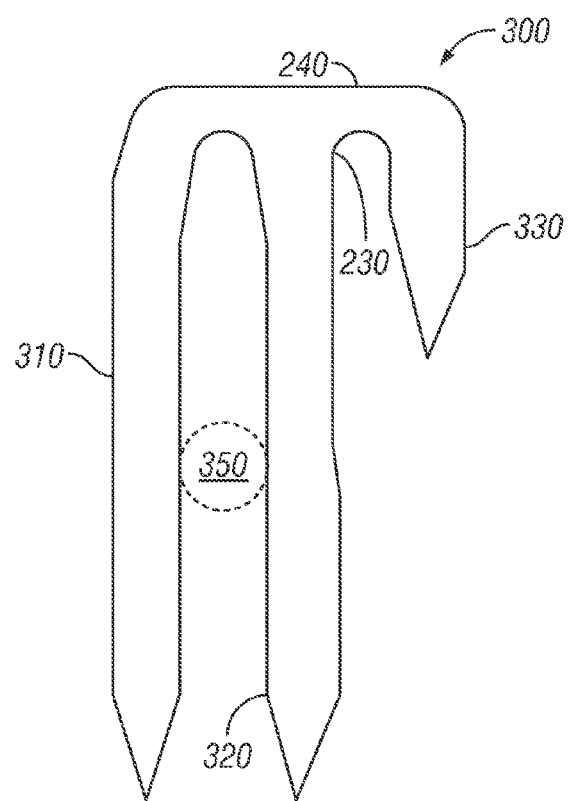
FIG. 3: A side view of another embodiment of a the "E" shaped vector compression anchor (300) is shown, which is characterized by two long prongs (310, 320) and one short prong (330). A cross section (350) of an example of a polymeric cored braided suture (110) is indicated in phantom in order to illustrate the a close or tight fit between the prongs (310, 320) and arch (230) of the vector compression anchor (300) and a polymeric cored braided suture (110).

The vector compression anchor (300) of FIG. 3 is a variation of the basic anchor (200) of FIG. 2, with the primary exception that the anchor (300) decouples the need to maintain optimal tension in the suture (110) while simultaneously providing optimal securement to the bone. As shown in FIG. 2, the prongs (210, 220) of a basic anchor (200) are equal in length. Consequently, a suture (110) cannot be wound around the middle prong (220) unless at least one outside prong (210) is not yet driven into the bone (120). However, in order to secure the basic anchor (200) into the bone (120), all three prongs (210, 220) must be driven into the bone at the same time. It is difficult decouple the two actions and thereby achieve optimization of the two goals.

The embodiment of FIG. 3, however, permits tensioning of the suture and positioning of the anchor to be independently achieved, thereby making it quite possible to achieve optimization of both goals. Anchor (300) is configured to enable all three prongs to be simultaneously driven into the while continuously maintaining optimal tension in the suture. More particularly, in the embodiment shown, the anchor (300) includes a first outer prong (310), a middle prong (320) that is substantially the same length as the middle prong (320), and a second outer prong (330) with a length that is shorter than the middle prong (320). As such, the first outer prong (310) and the middle prong (320) can be driven partially into bone to secure the position of the anchor (300) while still permitting a suture (110) to be wrapped around the middle prong (320). Consider the following exemplary steps for deployment of a vector compression anchor (300) during a surgical procedure (as, for example, shown in FIG. 7):

1. The suture (110) can be threaded between the long outer prong (310) and the long inner prong (320).
2. The two prongs (310, 320) can be driven partly into the bone (120) at a depth that is adequate to secure the prongs (310, 320) (e.g., such that the anchor resists removal from the bone), yet shallow enough to allow wrapping of the suture (110) around the long inner prong (320) and through the space between the long inner prong (320) and the short outer prong (330).
3. The vector compression anchor (300) can then be driven the remainder of the way into the bone, thereby securing the vector compression anchor (300) and the suture (110) without having to compromise placement of or reposition the two long prongs (310, 320), nor allow a release of tension in the cable (110).

Figure 7:
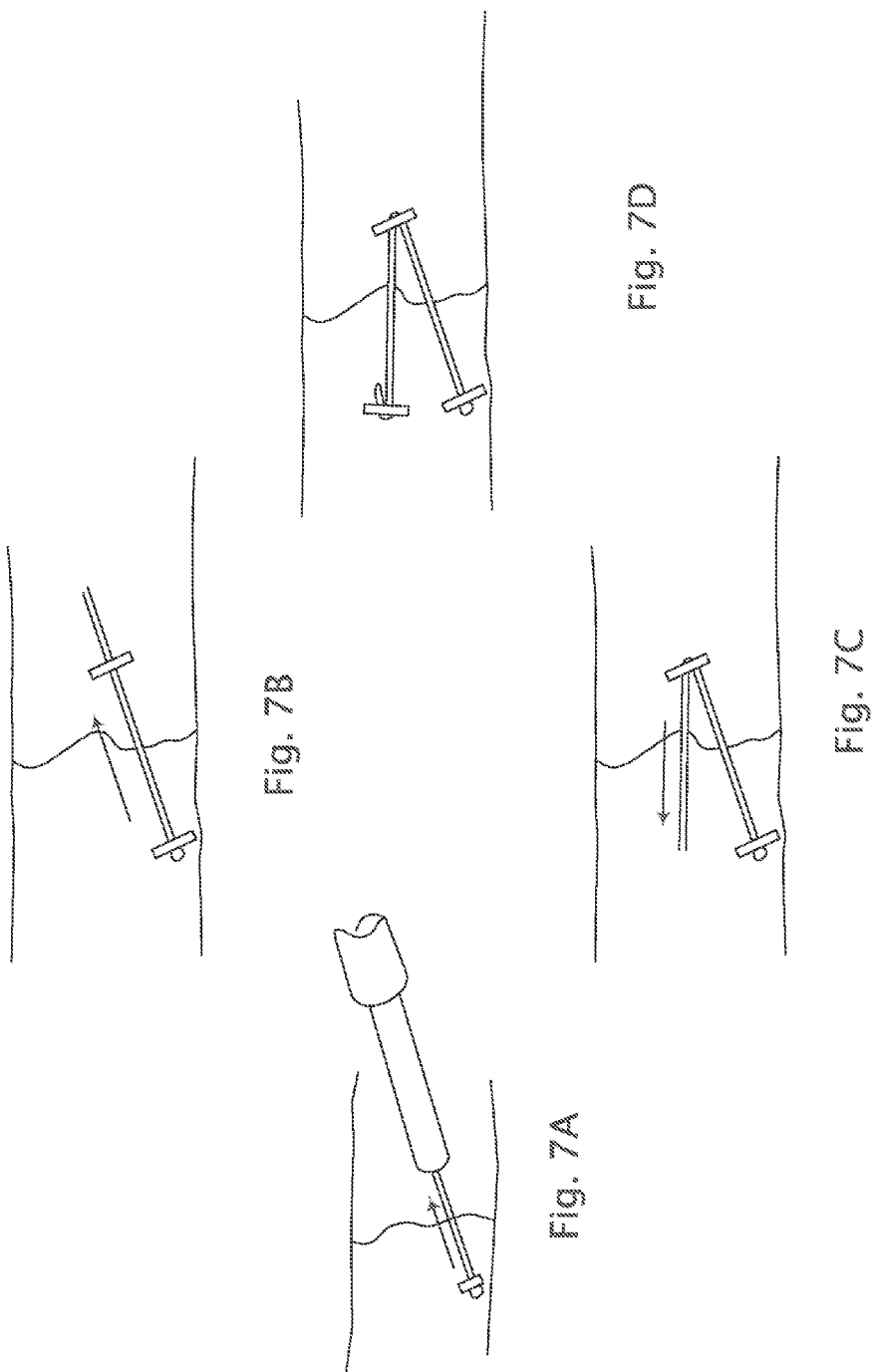
FIG. 7: A step-by-step process for constructing the exemplary pattern of FIG. 1 using the deployment instrument (600) of FIG. 6 is shown in FIGS. 7A-7D.

At least some of the present vector compression anchors and/or systems are thus configured to permit a direct line of force to be maintained between one vector compression anchor (e.g., 300) and the next in the "chain" such as is shown in FIGS. 1 and 7.

Additional embodiments of the present vector compression anchors are shown in FIGS. 4-5. FIG. 4 shows two embodiments (400 and 410) of the present vector compression anchors. FIGS. 4A and 4C illustrate perspective and top views, respectively, of a flat vector compression anchor (400), the advantages and deployment of which were discussed above. FIGS. 4B and 4D illustrate perspective and top views, respectively, of a curved vector compression anchor (410) that is substantially similar to anchor (400) with the primary exception that the bridge of anchor (410) is curved whereas the bridge of anchor (400) is straight.

In the embodiment shown, the curve of the bridge of anchor (410) can include an arc of a conic section (e.g., a circle, ellipse, parabola, and/or the like), and/or may be otherwise curved. In the embodiments shown, the bridge and prongs of each of the anchors (400 and 410) comprises a chamfered and/or a beveled edge (415) such as, for example, adjacent the arch or space between prongs to mitigate stress concentrations in and/or on the anchor and/or a tensioned suture disposed between two prongs of the anchor.

Figure 4A:
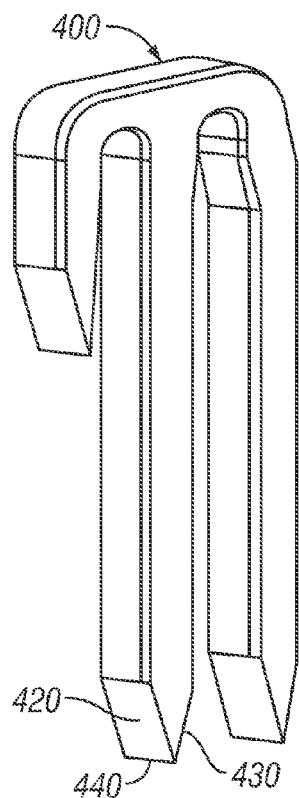
FIG. 4: This figure shows two additional embodiments of the "E" shaped vector compression anchor (300). The first embodiment, perspective and bottom views of which are shown in FIGS. 4A and 4C, respectively, is flat (400), while the second embodiment, perspective and bottom views of which are shown in FIGS. 4B and 4D, respectively, is curved (410). The curve of the second embodiment is an arc of a conical section (e.g., a circle, ellipse, or parabola).

In the embodiments shown, the prongs of anchors (400 and 410) each has a proximal end (at the bridge) and a distal end (extending away from the bridge), and at least one (e.g., all) of the distal ends comprise cutting portions configured to be inserted into bone. As shown in FIG. 4A, at least one (e.g., two) cutting portion of anchor (400) comprises first and second faces (420 and 430) that taper relative to each other to define a cutting edge (440). In the embodiment shown, the cutting edge (440) is perpendicular to a central, longitudinal axis of the prong; however, in other embodiments, the cutting edge may be disposed at a non-perpendicular angle relative to a longitudinal axis of the prong (e.g., such that, during insertion, a portion of the cutting edge contacts the bone before other portions of the cutting edge). In the embodiment shown, each cutting edge of anchor 400 lies in a plane that substantially bisects the prong on which it is disposed (e.g., the cutting edge lies substantially centered on the distal end of the prong), however, in other embodiments, the cutting edge may be offset or rotated relative to a plane that bisects the respective prong. In the embodiment shown, the faces (420, 430) that define each cutting edge (440) are substantially symmetrical (have equal lengths measured along a longitudinal axis of the prong); however, in other embodiments, the first and second faces may not be symmetrical (e.g., as in prong (330) of anchor 300).

Figure 4B:
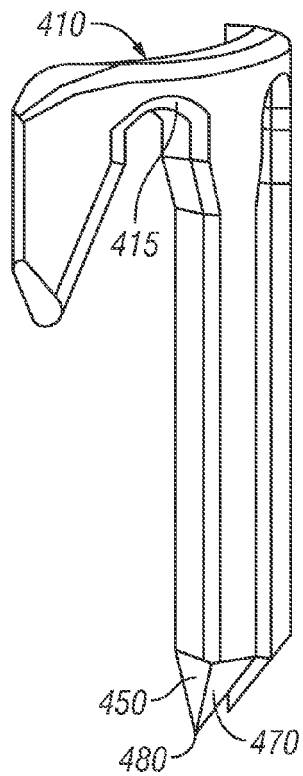
Figure 4C:
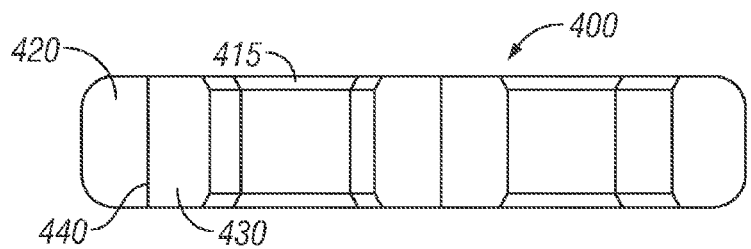
Figure 4D:
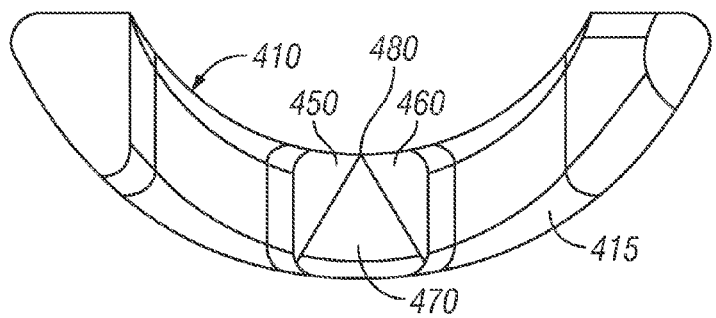

The curved embodiment of the anchor (410) shown in FIG. 4B includes another example of a cutting portion that is suitable for at least some of the present embodiments. In the embodiment shown, the cutting portion comprises first, second, and third faces (450, 460, 470) that taper relative to each other to define a cutting point (480). In other embodiments, such a cutting point can be defined by any number of faces (e.g., 1, 2, 3, 4, 5, or more faces). In this embodiment, the faces that define the cutting point each extend along a direction from the proximal end to the distal end of the prong a substantially equal distance, however, in other embodiments, one face of the cutting portion may extend a longer such distance than another face (e.g., similar to as described above). In the embodiment shown, the cutting point is not centered on the prong on which it lies (e.g., as shown), however, in other embodiments, the cutting point may be substantially centered on the distal end of the prong.

Figure 5A:
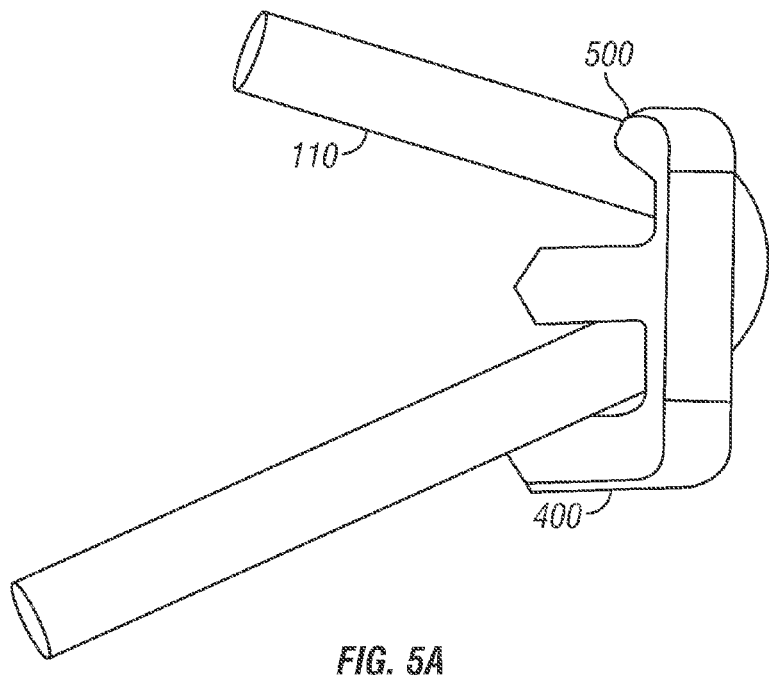
FIG. 5: Illustrates a comparative implementation of the two embodiments of FIG. 4. The notable differences in their relative performance can be seen by comparing the two regions indicated (500, 510), wherein the short prong (330) of the flat vector compression anchor (400) in FIG. 5A can be seen crimping or cutting into the polymeric cored braided suture (110), while the short prong (330) of the curved vector compression anchor (410) in FIG. 5B clears it.
Figure 5B:
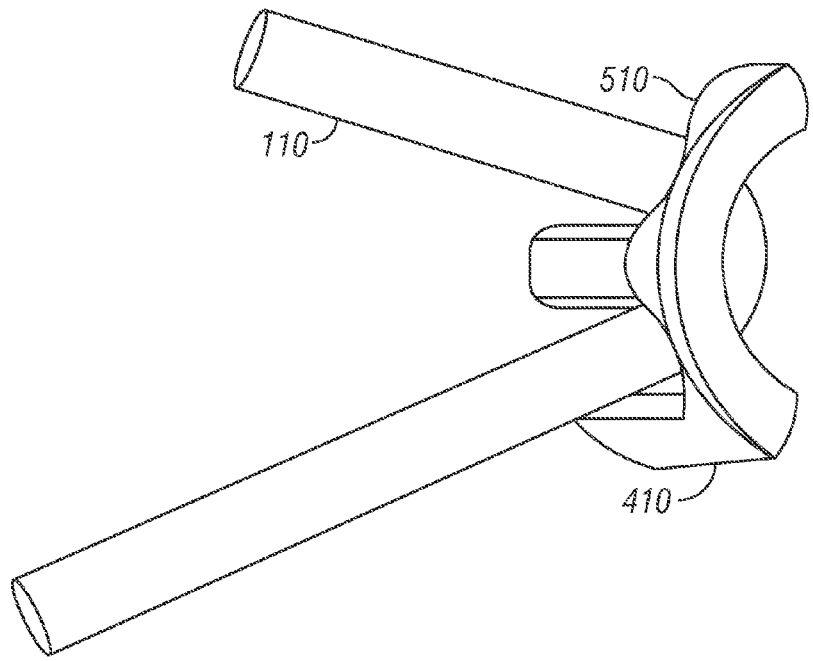

Certain advantages of a curved vector compression anchor (410) over its flat counterpart (at least between curved and flat anchors having similar widths between their respective outer prongs) can be seen by considering the comparisons shown in FIGS. 5A and 5B. Because the bridge (240) of the curved vector compression anchor (410) is curved, the distances between the middle prong and the outer prongs are larger than a flat anchor of similar width, such that the curved anchor can straddle the suture (110) along a line more closely aligned with the suture's diameter. The flat anchor (400), on the other hand, straddles the suture (110) along a line more angled with respect (farther from parallel) to the suture's diameter. The straddling length across which the flat anchor (400) contacts the suture (110) is longer than the straddling length across which the curved anchor (410) contacts the suture (110). As described above with reference to FIG. 3, the prong spacing between each adjacent pair of prongs (e.g., 320, 330) is roughly the diameter of the suture (110) for which an anchor has been constructed, such that the anchor can hold the suture as securely as possible without compromising the structure of the suture. Thus, the shorter straddling length provided by the curved compression anchor (410) can be accommodated by the prong spacing. The longer length of the flat anchor (400) embodiment may be relatively more-susceptible to secondary problems such as cutting into the suture (110) structure. Consequently, the present curved compression anchors (e.g., 410) may provide all the advantages of the flat compression anchor (400) as well as providing a better hold on the suture (110) while being less susceptible to compromising the structure of the suture.

Figure 6:
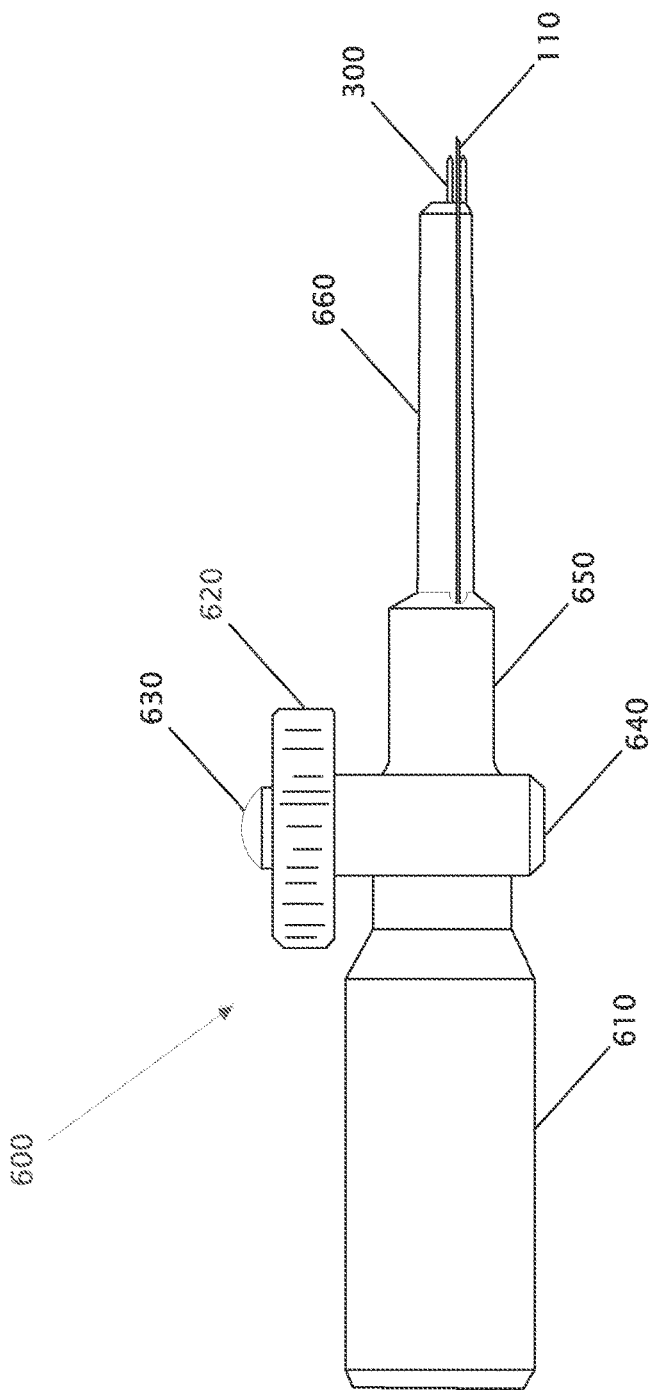
FIG. 6: Illustrates an exemplary embodiment of a deployment instrument (600) for housing and/or deploying various sutures (e.g., 110) and anchors (e.g., 100, 200, 300, 400, 410) in a surgical environment.

An exemplary deployment instrument (600) is shown in FIG. 6. As discussed above, an appropriate deployment instrument (600) can be configured to have some or all of the following attributes:

1. be packaged as an easily handled compact unit which may be designed for endoscopic use;
2. have simple controls (e.g., to be workable in a surgical environment);
3. be able to drive the anchors in a controlled condition or manner (e.g., in a controllable and/or smooth fashion without compromising suture tension);
4. be able to thread and/or tension the suture (e.g., between and/or amongst one or more anchors) to attain a desired compressive force (e.g., across a bone fracture);
5. be able to set the compressive force so that the suture does not slip relative to the anchors; and/or
6. incorporate an interchangeable and/or disposable cartridge (e.g., an anchor magazine and/or suture drum) that attaches to a power unit and that can house the suture and/or anchors.

In the embodiment shown, the exemplary deployment instrument (600) is configured to house a length of the suture (110) and a set of up to 5-6 vector compression anchors (300). In this embodiment, the deployment instrument (600) is also configured to drive the anchors (e.g., 100, 200, 300, 400, 410) into the bone effectively, position the suture (110) between the anchors, enable a user to adjust and apply the a desired level of tension in the suture (110), set the anchor while maintaining the desired level of tension, and effect a smooth transition to setting each subsequent anchor in an any of various exemplary patterns, such as is shown in FIGS. 1 and 7.

In the embodiment shown, the instrument (600) comprises a generally cylindrical structure that is configured to incorporate (e.g., removably) an anchor magazine (660) for housing a plurality of (e.g., up to 5-6) anchors (e.g., 100, 200, 300, 400, 410) (e.g., up to 5-6 anchors). In this embodiment, the deployment instrument (600) also comprises a suture drum (650) that houses a length of the suture (110), such as, for example, on a spool that may be rotated to release or retract the suture. The suture drum (650) and anchor magazine (660) may be coupled together so as to be simultaneously removable from the instrument (600), or may be independently removable from the instrument (600). In the embodiment shown, the instrument (600) further comprises an impulse motor (610) that is configured and can serve to drive the anchors (e.g., 100, 200, 300, 400, 410) into the bone, such as, for example, in a hammer-like fashion in which the impulse motor (610) or an extension thereof impacts and/or vibrates the bridge of the anchor to facilitate insertion of the anchor into bone (e.g., via the force of the impulse motor (610) and/or the force of a user applying a force to the instrument (600) in the direction of insertion). For example, in the embodiment shown, impulse motor (610) can be configured to impact a single anchor multiple times (e.g., at a frequency of greater than any one of, or between any two of, 2000 Hz, 3000 Hz, 4000 Hz, 5000 Hz, and/or 7500 Hz) to drive the anchor into the bone.

In the embodiment shown, the instrument (600) also comprises a tensioning knob (620) that can be rotated by a user to apply tension to the suture, and a ratchet mechanism (640) that is coupled to the tensioning knob (620) and/or suture drum (650) to restrict release of the suture (e.g., by preventing rotation of a spool of the suture drum (650) in one direction) and thereby maintain tension in the suture, such that tension can be applied to and maintained in the suture (110) via the tensioning knob (620) and ratchet mechanism (640). In the embodiment shown, the instrument (600) also includes a tension release button (630) that coupled to the ratchet mechanism (640) such that, when the suture (110) has been adequately secured by an anchor, the tension release button (630) can be pressed in order to release tension in the suture (110) between the anchor and the instrument (600) to proceed to the next step (e.g., placement and insertion of a subsequent anchor).

The step-by-step process for one example of a method of constructing the exemplary pattern of FIG. 1 using the deployment instrument (600) of FIG. 6 is shown in FIGS. 7A-7D. The deployment process is as follows:
1. As illustrated in FIG. 7A:
   a. A surgeon can trigger the impulse motor (610) to set the first anchor (e.g., 300).
   b. The suture (110) can be fed from suture drum (650) and/or anchor magazine (660) and across the fracture line to the next deployment site.
2. As illustrated in FIG. 7B:
   a. The long outer prong (310) and long inner prong (320) of the anchor (e.g., 300) can be partially driven into the bone to a depth such that the short outer prong (330) allows the suture (110) to pass beneath it (e.g., such that the outer prong does not contact the bone and the suture can be positioned between the long outer prong and the inner prong).
   b. The surgeon can adjust and/or set a tension of the suture (110) with the tensioning knob (620) of the deployment instrument (660).
3. As illustrated in FIG. 7C:
   a. While holding suture (110) under tension, a sleeve in the instrument (660) can rotate suture (110) around the short outer prong (330).
   b. The suture (110) can then be completely secured by driving the all three prongs of the anchor (e.g., 300) as deep as possible into the bone (e.g., such that the suture is secured between the long inner prong and the short outer prong).
   c. Tension in the suture (110) between the secured anchor (e.g., 300) and the deployment instrument (600) can be released via the tension release button (630).
4. As illustrated in FIG. 7D: The above steps can be repeated until a desired "stitch" pattern across the fracture has been constructed. Most commonly, one of an I-, V-, N-, or W-shaped suture pattern will likely be employed.

While several illustrative embodiments have been shown and described, numerous variations and alternate embodiments will occur to those skilled in the art, and can be made without departing from the spirit and scope of the invention as defined in the appended claims.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices, kits, and methods are not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A surgical anchor operable for securing surgical cable, said surgical anchor comprising:
   an "E" shaped staple having three prongs and a bridge;
   wherein said three prongs are substantially parallel to each other; and
   wherein said bridge is unitary with and substantially perpendicular to each of said three prongs; and
   wherein each of the three prongs has a proximal end coupled to the bridge and a distal end extending away from the bridge, and the distal ends of at least two of the prongs comprise cutting portions configured to be inserted into bone,
   the cutting portion of at least one of the prongs comprises at least a first face and a second face each having a proximal end and a distal end, the distal end of the first face abutting the distal end of the second face to define a cutting edge or a cutting point.

2. The surgical anchor as in claim 1 wherein said three prongs include:
   a first outer prong, a middle prong, and a second outer prong;
   a first space between the first outer prong and the middle prong, said first space having a first width between the first outer prong and the middle prong, and a first arch defined by the first outer prong, the middle prong and the bridge; and
   a second space between the second outer prong and the middle prong, said second space having a second width between the second outer prong and the middle prong, and a second arch defined by the second outer prong, the middle prong and the bridge;
   wherein said first width is substantially equal to said second width.

3. The surgical anchor of claim 2, where at least one of the bridge and a prong comprises an edge that is chamfered or beveled.

4. The surgical anchor of claim 3, where the edge is adjacent to one of the first and second spaces between prongs.

5. The surgical anchor of claim 1, where the distal ends of all three of the prongs comprise cutting portions configured to be inserted into bone.

6. The surgical anchor of claim 1, where the cutting portion of the at least one of the prongs comprises the first face and the second face that are tapered relative to each other to define the cutting edge.

7. The surgical anchor of claim 6, where the cutting edge is substantially perpendicular to the prong.

8. The surgical anchor of claim 6, where the cutting edge lies in a plane that substantially bisects the respective prong.

9. The surgical anchor of claim 6, where the first and second faces are not symmetrical.

10. The surgical anchor of claim 6, where the first and second faces are symmetrical.

11. The surgical anchor of claim 1, where the cutting portion of the at least one of the prongs further comprises a third face, and where the first, second, and third faces taper relative to each other to define the cutting point.

12. The surgical anchor of claim 11, where the cutting point is substantially centered on the distal end of the prong.

13. The surgical anchor of claim 1, where at least one of the prongs has portion in which a transverse dimension of the prong decreases in a direction from the proximal end to the distal end.

14. The surgical anchor of claim 1, where at least one of the prongs has a portion in which a transverse dimension of the prong increases in a direction from the proximal end to the distal end.

15. A kit comprising:
a plurality of surgical anchors of claim 1; and
a length of suture having a solid core surrounded by a braided jacket.

16. The kit of claim 15, further comprising:
a housing within which the surgical anchors and suture are disposed.

17. The surgical anchor of claim 1, where:
the first face comprises a first planar surface,
the second face comprises a second planar surface, and
the first face is distinct from the second face.

* * * * *